United States Patent [19]
Yoshpa

[11] Patent Number: 5,882,647
[45] Date of Patent: Mar. 16, 1999

[54] AQUATIC ANIMAL TREATMENT METHOD AND COMPOSITION CONTAINING CAJEPUT OIL

[75] Inventor: Michael Yoshpa, Chalfont, Pa.

[73] Assignee: Aquarium Pharmaceuticals, Inc., Chalfont, Pa.

[21] Appl. No.: 676,868

[22] Filed: Jul. 2, 1996

[51] Int. Cl.$^6$ .......................... A61K 35/78; A61K 31/23; A61K 31/20
[52] U.S. Cl. .................. 424/195.1; 514/552; 514/558; 514/937; 514/938
[58] Field of Search ................ 424/195.1; 514/558, 514/552, 937, 938

[56] References Cited

U.S. PATENT DOCUMENTS

| | | | |
|---|---|---|---|
| 4,282,828 | 8/1981 | Johnson | 119/215 |
| 4,363,290 | 12/1982 | Kunz et al. | 119/231 |
| 4,500,510 | 2/1985 | Goldstein | 424/195.1 |
| 5,009,890 | 4/1991 | DiPippo | 424/195.1 |
| 5,156,766 | 10/1992 | Behan et al. | 252/312 |

FOREIGN PATENT DOCUMENTS

| | | |
|---|---|---|
| 62-89607 | 4/1987 | Japan . |
| 2-53876 | 2/1990 | Japan . |
| 4-360839 | 12/1992 | Japan . |

OTHER PUBLICATIONS

Nguyen Duy Cuong et al, "Antibacterial Properties of Vietnamese Cajuput Oil," J. Essent. Oil Res., 6, pp. 63–67 (Jan./Feb. 1994).

Pham Truong Thi Tho et al., "Action Pharmacologique de L'Essence Du Tram," Revue Pharmaceutique, pp. 76–85 (1985).

Definition for "cajeput oil" and eucalyptol, The Condensed Chemical Dictionary, Eighth Ed., Rev. B.G. Hawley, Van Nostrand Reinhold Company, New York, pp. 151–152, 375 (1971).

J.B. Lowry, "A New Constituent of Biogenetic, Pharmacological and Historical Interest from *Melaleuca cajeputi* Oil," Nature, 241, pp. 61–62 (Jan. 5, 1973).

J.C. Maruzzella et al., "The in Vitro Antibacterial Activity of Oils," Journal of the American Pharmaceutical Association, XLV, 6, pp. 378–381 (Jun. 1956).

Marking et al., The Progressive Fish–Culturist, 56:225–231. 1994.

Lawless, The Illustrated Encyclopedia of Essential Oils, Barnes & Noble, Inc., p. 170. 195.

*Primary Examiner*—David M. Naff
*Assistant Examiner*—Janet M. Kerr
*Attorney, Agent, or Firm*—Panitch Schwarze Jacobs & Nadel, P.C.

[57] ABSTRACT

A method of treating an injured or diseased aquatic animal by adding an emulsion of cajeput oil to water containing the aquatic animal is disclosed. Effective amounts of cajeput oil which promote recovery from bacterial or fungal diseases, or from wounds, abrasions, or burns, range from 0.001 ml to 1 ml of cajeput oil per day per 10 gallons of water. The cajeput oil emulsion can also contain 0.01% to 20% of an emulsifier, and up to 5% of a defoamer.

23 Claims, No Drawings

AQUATIC ANIMAL TREATMENT METHOD AND COMPOSITION CONTAINING CAJEPUT OIL

FIELD OF THE INVENTION

The present invention is directed to the therapeutic and prophylactic treatment of aquatic animals and more particularly, to the treatment of fish and other aquatic animals with cajeput oil.

BACKGROUND OF THE INVENTION

Fish diseases and injuries are not only detrimental to the physiological well being of live fish, but also can adversely affect the physical appearance of otherwise viable fish. The prevention, control and treatment of fish diseases and fish injuries is particularly important for fish that are kept in artificial or confined environments such as aquariums or ponds, such as ornamental ponds or aquaculture ponds.

Fish that are netted, handled or otherwise placed in stressful situations, e.g., under low oxygen, high carbon dioxide, contaminated water or fluctuating temperature conditions, become more vulnerable to disease, such as those of bacterial or fungal origin. When fish are transported in high concentrations and/or in small volumes of water, they are often subject to trauma or injury such as being scraped, lacerated, bitten and otherwise wounded. Such shipping conditions may also expose fish to contaminated water, e.g., from natural waste products of fish and from decaying food and dead fish. Contaminated water is also an environment favoring the growth of pathogens that cause fish diseases.

The term "fish diseases" and other similar terms as used herein are intended to cover not only fish diseases of bacterial or fungal origin, but also fish suffering from, damaged by, or afflicted with trauma or injuries such as wounds, e.g., lacerations, tears and bites, as well as scrapes, abrasions, burns or the like. Rapid healing of such injuries is often slowed, delayed or precluded by the presence of pathogenic microorganisms in the water environment harboring the fish or in the injured skin, tissue or other like part of the fish.

Fish disease therapies that avoid the use of potent drugs or chemicals with adverse side effects or that avoid the necessity for precise dosing requirements are desirable for fish in confined environments. While isolation and treatment only of the specific diseased or injured fish is preferred, as a practical matter, such isolated treatment is not often possible, resulting also in exposure of healthy fish to the treatment. Consequently, treatment of individual diseased fish usually entails exposure of healthy fish and all other beneficial organisms in the environment to the active ingredient as well. For this reason, therapeutic treatments for diseased fish that utilize naturally derived substances which are not injurious to other aquatic animals or plants also present in the water are particularly preferred.

The treatment of damaged fish tissue in living fish with *aloe vera* is described by Goldstein in U.S. Pat. No. 4,500,510, assigned to the assignee of the present invention. The prevention and treatment of bacterial diseases in fish with eucalyptus extract is described in Japanese Patent Publication 04-360839. Eucalyptus extract is a complex mixture obtainable from leaves of Eucalyptus species trees, and the primary component of eucalyptus oil is 1,8-cineole, sometimes also called eucalyptol (about 70–85%).

The present invention is based on the unexpected discovery that cajeput is highly efficacious in the therapeutic treatment of fish and other aquatic animals. Cajeput oil, obtainable from leaves of the tree *Melaleuca cajuputi, M. leucadendron* and other species of Melaleuca (Myrtaceae) contains a large number of components, most of which are terpenoids and one major component being 1,8-cineole (about 39%). Although cajeput oil is known for its therapeutic properties in treating humans (see, e.g., Cuong et al., "Antibacterial Properties of Vietnamese Cajuput Oil," J. Essent. Oil. Res., 6, pp. 63–67 (January 1994)), its use in treating fish has not previously been reported or suggested.

SUMMARY OF THE INVENTION

According to the present invention, a therapeutic and prophylactic method for treating fish and other aquatic animals comprises administering cajeput to an aquatic animal in an amount effective to promote recovery of such a diseased aquatic animal.

Another aspect of the invention is a composition for the treatment of fish and other aquatic animals which comprises an aqueous mixture containing cajeput oil.

The method and composition are useful for treating living fish of all types and species and other aquatic animals afflicted with, subjected to or susceptible to bacterial disease, fungal disease or injuries such as wounds, abrasions, burns and the like. The cajeput is preferably administered by introducing an aqueous emulsion comprising cajeput oil and water into the water containing the aquatic animal to be treated.

DESCRIPTION OF THE PREFERRED EMBODIMENTS

The active ingredient for the aquatic animal treatment method and composition of this invention is cajeput. As used herein, "cajeput", sometimes called cajuput or cajeputi or oil of tràm, is the substance that is obtainable from the low growing shrub-like tree of the Melaleuca species, preferably *Melaleuca cajuputi* Powell (Myrtaceae) or *Melaleuca leucadendron* L. (Myrtaceae), which is indigenous to Southeast Asia. References to cajeput in this disclosure are intended to include cajeput oil, the most commonly available form of cajeput. Cajeput oil is typically produced by the known technique of hydrodistillation (steam distillation) of fresh leaves and twigs of the Melaleuca species. It is important to note that the cajeput utilized in this invention is a complex mixture of components normally found in cajeput oil, rather than a single component fractionally distilled and separated from cajeput, e.g., 1,8-cineole. Cajeput oil is produced in commercial quantities in Southeast Asia, particularly Vietnam, and is readily available from commercial suppliers of naturally derived food and cosmetic oils and extracts.

Cajeput oil is preferred in view of its commercial availability, but other forms of cajeput may also be used, e.g., cajeput extract in a liquid (solvent or another oil), cajeput adsorbed onto or absorbed into a solid carrier or substrate, or cajeput associated with other vehicles, provided that such vehicles are compatible with the administration of the cajeput into water harboring the aquatic animal to be treated and do not adversely affect the aquatic animal being treated or other beneficial aquatic life in the water.

Cajeput oil may be introduced directly into water containing aquatic animal to be treated, but it should be noted that cajeput oil is relatively insoluble in water. Consequently, direct addition of cajeput to water requires an effective means of dispersion, e.g., high speed or high shear mixing, and such intensive dispersion is preferably carried out in a localized region in the absence of the aquatic animal being treated to avoid injury; a metering/mixing pump or an inline mixer, e.g., mixing valve or orifice, may be used to accomplish the direct dispersion of cajeput in water.

A preferred technique for administering the cajeput in this invention involves the use of an aqueous mixture or dispersion of cajeput that is introduced into the water harboring the aquatic animal to be treated. The aqueous mixture or dispersion of cajeput is preferably introduced to the water containing the aquatic animal in a manner that ensures further mixing of the mixture or dispersion in the water. Such mixing should provide relatively uniform distribution of the cajeput throughout the water, so that the fish or other aquatic animals being treated are continually exposed to the cajeput as they swim in the water. In a small volume of water such as a fish hobbyist's fish aquarium, normally circulation of the water, e.g., via aeration of the water, typically provides good mixing and distribution of the cajeput through the aquarium water. If there is no filter pump or aerator or if circulation of the aquarium water is otherwise inadequate, the mixture or dispersion of cajeput may be simply poured in and the aquarium water gently stirred. For larger volumes of water harboring the fish or other aquatic animals to be treated, additional mechanical mixing may be required.

With respect to the aqueous mixture or dispersion containing cajeput used to treat small volumes of water, e.g., aquariums containing less than about 50 gal (190 l), vigorous shaking of cajeput and water in a sealed container of less than about 1 gal (3.8 l) is normally sufficient to provide an aqueous cajeput mixture suitable for use by the typical fish hobbyist. The aqueous cajeput mixture may then be introduced into the aquarium water by simply pouring the mixture into the aquarium.

A preferred cajeput composition of this invention is an aqueous mixture containing from about 0.1% to about 20% cajeput, more preferably from about 0.5% to about 10% cajeput and most preferably about 1% to about 5% cajeput, all percentages being by volume.

The aqueous cajeput-containing composition preferably contains an emulsifier in an amount sufficient to emulsify the cajeput oil in water, to provide a relatively stable emulsion. Preferred emulsifiers (sometimes called surfactants) are those which are nontoxic and noninjurious to the aquatic animal being treated, and these include food grade emulsifiers which are widely available.

Nonionic emulsifiers are especially preferred, with Crovol™ PK-70 nonionic emulsifier (Croda Inc., Parsippany, New Jersey, U.S.A.) being a highly preferred nonionic emulsifier that is water soluble.

The amount of emulsifier used to provide emulsification of the cajeput oil in water is generally not critical, and the concentration of emulsifier may range from about 0.01% to about 20%, more preferably about 0.1% to about 5%, all percentages being by volume. For emulsifiers or surfactants that are normally not liquid, the numerical concentration ranges just noted may be used, with percentages being by weight based on the volume of aqueous emulsion.

Other adjuvants besides emulsifiers may also be used, such as antifoams or defoamers, antioxidants, preservatives, coloring agents and the like. The adjuvants are typically present in the aqueous cajeput composition in minor amounts, i.e., less than about 5% by volume and preferably less than 1% by volume. All such adjuvants should be noninjurious and nontoxic to the fish and other aquatic animals being treated, as well as to other beneficial aquatic organisms present in the water along with the aquatic animal being treated, such as various types of invertebrates and plants.

A particularly preferred stable emulsified aqueous cajeput composition is as follows:

| | |
|---|---|
| cajeput oil | 1% by volume |
| emulsifier | 1% by volume |
| defoamer | 0.2% by volume |
| deionized water | 97.8% by volume |

The emulsifier is preferably Crovol™ PK-70 nonionic emulsifier (Croda Inc.) and the defoamer is preferably FG-10 antifoam (Dow-Corning Corp., Midland, Michigan, U.S.A.), the latter serving to control foaming otherwise caused by the emulsifier. The composition may be prepared by vigorously mixing the cajeput oil, emulsifier and defoamer in the deionized water, to produce an aqueous emulsion that is stabilized against separation of the cajeput oil from the aqueous phase. Such mixing may be carried out with a mechanical mixer or by manual shaking.

An aqueous mixture containing cajeput, e.g., 1% by volume, can be prepared without the emulsifier and defoamer, but such an aqueous mixture must be vigorously shaken (for 1–5 minutes) or mechanically agitated prior to use to disperse the cajeput oil uniformly throughout the aqueous phase.

Cajeput has been found to be extremely effective in providing complete recovery of afflicted fish or other aquatic animals even when used at low concentrations. For this reason, the present invention includes, as a preferred treatment, introducing cajeput into the water in which the afflicted aquatic animals are normally harbored or confined.

In the treatment method of this invention, the cajeput is introduced into the water containing the fish or other aquatic animal to be treated in an amount of from about 0.001 ml (1 microliter) to about 1 ml, preferably from about 0.01 ml (10 microliters) to about 0.5 ml (500 microliters), per day per 10 gallons (37.8 liters) of water containing the aquatic animal (s) being treated; these amounts are based on the volume of cajeput per se. This amount may be added as a single dosage each day, as is preferred, or may be added in aliquots of the daily dosage throughout the day.

With the preferred aqueous emulsion composition described above containing 1% by volume cajeput, a highly preferred daily dosage rate is 5 ml of the aqueous emulsion per 10 gallons of water containing the aquatic animal(s) being treated.

The daily treatment dosage is continued for as long as is necessary to provide recovery. Typically, duration of the treatment is at least about three days to about two weeks. Disappearance of the outward, visible symptoms or signs of the disease, which signs may sometimes include animal behavior, affecting the fish or other aquatic animal normally indicates successful treatment and recovery of the aquatic animal from the disease. The treatment duration should desirably include continued daily dosages for about 2–5 days following apparent recovery, to prevent disease recurrence or secondary infection of healed wounds.

The recovery of the diseased aquatic animals, especially fish, from their affliction with the treatment method and composition of this invention has been observed to be much faster than the recovery, if the fish recover at all, that results without treatment in accordance with the present invention. Many fish diseases, such as "ragged fins", often cannot be successfully treated with commonly used fish medications, including antibiotics and "salt baths."

In the treatment method of this invention, factors such as water pH, hardness, alkalinity and the like do not appear to have any significant effect. The water may be fresh water or may be salt water, a factor normally determined by the fish or other aquatic animal species being treated. Water temperature is maintained within the range that is normally used for the animal species being treated.

The cajeput composition and treatment of this invention are effective for a broad range of bacterial and fungal diseases that typically afflict fish and other aquatic animals. Fish diseases that may be treated in accordance with this invention include bacterial fish diseases such as fin and tail rot, mouth fungus (often caused by the bacterium *Chondroceus columnaris*); fungal fish diseases (such as those caused by microorganisms of the genera Saprolegnia and Achyle); and the like. Many fish diseases, it should be noted, are caused by different bacterial or fungal pathogens that often exhibit similar symptoms, so identification of a specific bacterial or fungal pathogen is not usually possible from mere visual inspection of the symptoms on the fish. Since the cajeput treatment of this invention appears to have broad spectrum effectiveness against many fish diseases, precise identification of specific bacterial or fungal microorganisms causing the disease is not usually necessary.

The cajeput composition and treatment of this invention also enhance skin and tissue healing and promote such healing in injured fish or other aquatic animals. Common fish injuries include those resulting from netting, handling or confinement in closed or crowded environments like shipping containers or holding tanks, in particular injuries such as wounds, lacerations, bites from other fish or animals, abrasions, scrapes, burns and other similar damage to skin or tissue. The references herein to "diseased fish" or "diseased aquatic animals", as noted earlier, are intended to include injuries such as those just described.

The cajeput treatment and composition of this invention are remarkably effective in curing such difficult-to-treat fish diseases like ragged fins. It has been observed that the fish being treated appear to swim towards the region where the cajeput is introduced into the water, when the first cajeput dosage is administered.

The cajeput composition and treatment method of this invention may also be used as a prophylactic or hygienic treatment, to prevent disease or injury-susceptible fish or other aquatic animals from becoming afflicted. The treatment protocol and dosage rates to be used for prophylactic treatment are the same as those described above for the therapeutic treatment of diseased fish and other aquatic animals. For example, fish to be transported in shipping containers may be treated beforehand and during shipping according to this invention to prevent or minimize susceptibility to disease, including aggravation of injuries sustained before or during shipping. As with all medicaments, continuous long-term treatment is not generally recommended, since it creates the risk of developing resistant strains of pathogenic microorganisms that cannot be successfully controlled with the medicament.

The fish or other aquatic animals which may be treated according to this invention are typically aquatic animals held in a confined body of water such as a shipping container, holding tank, aquarium, pool or small pond. Although it is feasible to treat fish or other aquatic animals in large confined bodies of water, e.g., lakes or large ponds, or unconfined water such as streams, the large quantity of cajeput required in such situations is generally not economically practical.

It should be apparent that diseased fish or other diseased aquatic animals can be removed temporarily from their natural habitat of large bodies of water, into a small confined water body, specifically for treatment by the method of this invention and thereafter returned to their natural habitat.

It is also feasible to administer a cajeput-containing composition, e.g., an aqueous emulsion-containing cajeput oil or cajeput oil neat, to the fish or other aquatic animal via topical application to the affected sites on the aquatic animal. This technique, however, requires that the affected fish or aquatic animal be temporarily removed from water and does not lend itself to continuous treatment of the affected aquatic animal over a period of several days. Apparatus that may be used for direct administration of cajeput to fish is described by Johnson in U.S. Pat. No. 4,282,828 and by Kunz et al. in U.S. Pat. No. 4,363,290, both of which are hereby incorporated herein by reference.

Treatment of large numbers or concentrations of fish in breeding or aquaculture ponds, on the other hand, is intended to be included as an important application for the preferred method of this invention, in which cajeput is introduced into the water in which the fish are confined.

The present invention is applicable to the treatment of living fish and other living aquatic animals. The term "fish" as used herein has a wide sense covering various aquatic animals and including, without limitation, fish that are fresh water fish species, salt water ("marine") fish species, tropical fish species and cold water fish species. The fish may be adults, juveniles, hatchlings or embryos or combinations of these. The invention is also applicable to treating other aquatic animals besides fish such as amphibians, e.g., frogs and salamanders, reptiles, e.g., turtles, crustaceans, mollusks, whales, dolphins and the like that may be afflicted with fungal or bacterial diseases, including injuries, analogous to those described above for fish.

The following fresh water fish species have been treated with cajeput according to this invention:

| COMMON NAME | SCIENTIFIC NAME |
| --- | --- |
| Freshwater barracuda | Acestrorhynchus falcirostris |
| Iridescent shark | Pangasius sutchi |
| Silver dollar | Metynnis hypsauchen |
| Commmon goldfish | Carassius auratus |
| Elephant nose fish | Gnathonemus petersi |
| Discus | Symphysodon aequifasciata |
| Butterfly fish | Pantodon buchholzi |
| Striped anostomus | Anostomius anostoimus |
| none | Alestes chaperi |
| none | Arnoldichthys spilopterus |
| Cardinal tetra | Paracheirodon axelrodi |
| Neon tetra | Cheirodon innesi |
| Black tetra | Gymnocorymbus ternetzi |
| Indian knife fish | Notopterus chitala |
| Black wedge tetra | Hemigrammus pulcher |
| Bleeding heart tetra | Hyphessobrycon erythrostigma |
| none | Moenkhausia sanctae filomenae |
| Clown loach | Botia macracantha |
| none | Botia modesta |
| Rosy barb | Barbus conchonius |
| Sumatra barb | Barbus tetrazona tetrazona |
| Golden barb | Barbus schuberti |
| Cherry barb | Barbus titteya |
| Zebra danio | Brachydanio rerio |
| Red tailed black shark | Labeo bicolor |
| Red rasbora | Rasbora heteromorpha |
| Marbled hatchetfish | Carnegiella strigata |
| Leopard corydoras | Corydoras julii |
| Swordtail | Xiphophorus helleri |
| Platy | Xiphophorus maculatus |
| Flag cichlid | Aequidens curviceps |
| Convict cichlid | Cichlasoma nigrofasciatum |
| none | Labeotropheus trewavasae |

-continued

| COMMON NAME | SCIENTIFIC NAME |
| --- | --- |
| none | Pseudotropheus zebra |
| Angelfish | Pterophyllum scalare |
| Kissing gourami | Helostoma temmincki |
| Three-spot gourami | Trichogaster trichopterus |
| Common pufferfish | Tetraodon cutcutia |

The following salt water fish species have been treated with cajeput according to this invention:

| COMMON NAME | SCIENTIFIC NAME |
| --- | --- |
| Powder blue tang | Acanthurus leucosternon |
| Hippo tang | Paracanthurus hepatus |
| Yellow tang | Zebrasoma flavescens |
| Sailfin tang | Zebrasoma veliferum |
| Black triggerfish | Odonus niger |
| Picasso trigger | Rhinecanthus aculeatus |
| Bicolor blenny | Ecsenius bicolor |
| Mandarinfish | Synchiropus splendidus |
| Bicolor cherub | Centropyge bicolor |
| Flame angelfish | Centropyge loriculus |
| King angelfish | Holacanthus passer |
| Firefish | Nemateleotris splendida |
| Birdmouth wrasse | Gomiphosus coeruleus |
| Leopard moray | Gymnothorax tesselatus |
| White-spotted boxfish | Ostracion meleagris |
| Common clownfish | Amphiprion ocellaris |
| Salmon clownfish | Amphiprion perideraion |
| Maroon clownfish | Premnas biaculeatus |
| Blue damselfish | Abudefduf cyaneus |
| Yellow-tailed damselfish | Chromis xanthurus |
| Humbug | Dascyllus aruanus |
| Royal gramma | Gramma loreto |
| Black-saddled puffer | Canthigaster valentini |
| Lionfish | Pterois volitans |

The treatment method and cajeput composition of this invention not only provide beneficial and surprisingly effective results with the diseased fish or other diseased aquatic animal being treated, but are also highly safe and innocuous to other beneficial aquatic organisms, both flora and fauna, that may typically be present in the water with the treated aquatic animal.

The cajeput composition and treatment described for this invention may be used in combination with other medicaments or healing treatments, if desired, but such other medicaments or treatments are not necessary to obtain the highly efficacious, beneficial results provided by cajeput.

The present invention will now be described and explained further, by reference to the following specific, illustrative, non-limiting Examples.

EXAMPLE 1

Two adult fresh water barracudas (*Acestrorhynchus falcirostris*) with severe shipping injuries were treated with cajeput in this Example 1. The shipping injuries to these fish included multiple large wounds on the tip of the snout and skin abrasions.

The cajeput composition used in this treatment was an aqueous emulsion containing 1% by volume cajeput oil (obtained from Berje Co., Bloomfield, New Jersey U.S.A. as "cajeput oil rectified", 1% by volume Crovol™ PK-70 nonionic emulsifier (Croda Inc.), 0.2% by volume FG-10 antifoam (Dow-Corning Corp) and the balance being deionized water. The cajeput composition was added to the tank containing the fish, once per day, in an amount of 5 ml per 10 gallons (37.8 l) of water in the tank.

Total duration of the cajeput treatment was 7 days. The wounds were observed to close within 24 hours of beginning the treatment. Complete healing occurred after 5 days. Treatment was continued for 2 more days (after the fifth day) to prevent any secondary infection of the newly healed surfaces.

EXAMPLE 2

Twenty juvenile common fancy goldfish (*Carassius auratus*) having a severe case of "ragged fins" were treated with cajeput in this Example 2. The cajeput composition and dosage amount were identical to that described for Example 1.

Total duration of the cajeput treatment was 10 days. Fin regrowth was visibly apparent 2 days after initiation of the treatment, and complete recovery was observed after 10 days.

EXAMPLE 3

Fifteen adult blue damselfish (*Abudefduf cyaneus*) having various degrees of bacterial infection, characterized by whitish blotches all over the fishes' bodies, were treated with cajeput in this Example 3. The cajeput composition and dosage amount were identical to that described for Example 1.

Total duration of the cajeput treatment was 8 days. The blotches on the fishes' bodies were observed to have disappeared after 3 days, and complete recovery was evident after 8 days.

EXAMPLE 4

A three year old silver dollar (*Methynnis hypsauchen*) with a chronic case of "bacterial fin rot" was treated with cajeput in this Example 4 after several other treatments proved unsuccessful.

The fish was first treated separately with three well-known medications intended for treating fish: (1) nitrofurazone (60 mg/10 gal (38 l)/day) and furozalidone (25 mg/10 gal (38 l)/day); (2) tetracycline hydrochloride (250 mg/5 gal (19 l)/day); and (3) sodium sulfathiazole (332 mg/5 gal (19 l)/day), and sodium sulfamethazine (84 mg/5 gal (19 l)/day), and sodium sulfacetamide (84 mg/5 gal (19 l)/day).

Each of these treatments was administered separately over respective four-day periods, with no activated charcoal in the filter and with 25% of the aquarium water being replaced one day after the second and fourth daily dosages. The fish was also treated with eucalyptus oil using a composition, dosage rate, and treatment duration similar to that described for cajeput in Example 1 except that eucalyptus oil was substituted for cajeput. After each of these treatments, there was no noticeable improvement, and the fish had only short "stumps" instead of the normal fins.

The cajeput treatment utilized the composition and dosage amount described for Example 1. Total duration of the cajeput treatment was 14 days. Fin regrowth was visible two days after initiation of the cajeput treatment, and complete recovery was evident after 14 days. The impressive recovery provided in this Example is particularly illustrative of the unexpected and surprising effectiveness of the method and cajeput composition of this invention, especially since the conventional fish treatments and use of eucalyptus oil failed to work.

EXAMPLE 5

Five adult Sumatra barbs (*Barbus tetrazona tetrazona*) having a fungal infection were treated with cajeput in this Example 5. The cajeput composition and dosage amount were identical to that described for Example 1.

Total duration of the cajeput treatment was 10 days. Four days after initiation of the treatment, the fungal "tufts" were observed to have disappeared, and complete recovery was evident after 10 days.

EXAMPLE 6

Three African clawed frogs (*Xenopus laevis*), which are aquatic frogs that can be maintained in fish tanks, having red-leg disease (believed to be caused by bacteria of the genus Aeromonas) were treated with cajeput in this Example 6. The cajeput composition and dosage amount were identical to that described for Example 1.

Total duration of the cajeput treatment was 15 days, after which time recovery was complete.

EXAMPLE 7

Two Axolotls, neotenic larvae of the salamander *Ambystoma mexicanum*, which are amphibians that can be maintained in fish tanks, having secondary bacterial infection of multiple wounds on their bodies were treated with cajeput in this Example 7. The cajeput composition and dosage amount were identical to that described for Example 1.

Total duration of the cajeput treatment was 8 days, and after this treatment period, recovery was complete.

EXAMPLE 8

One painted turtle (*Chrysemys picta*), which is an aquatic turtle that can be maintained in an aquaterrarium and spends much time in the water, having a secondary bacterial infection of a wound on the foot, was treated with cajeput in this Example 8. The cajeput composition and dosage amount were identical to that described for Example 1. The cajeput composition was introduced into the water pool inside the aquaterrarium.

Total duration of the cajeput treatment was 8 days, and after this period, recovery was complete.

The present invention may be embodied in other specific forms without departing from the spirit or essential attributes thereof and, accordingly, reference is made to the appended claims, rather than the foregoing specification, as indicating the scope of the invention.

I claim:

1. A method for treating a living injured or diseased aquatic animal which comprises adding to water containing the living injured or diseased aquatic animal an aqueous emulsion of cajeput oil in an amount effective to promote recovery of the living diseased or injured aquatic animal.

2. The method according to claim 1 wherein the living aquatic animal is afflicted with a disease selected from the group consisting of bacterial diseases and fungal diseases.

3. The method according to claim 1 wherein the living aquatic animal is afflicted with injuries selected from the group consisting of wounds, abrasions and burns.

4. The method according to claim 1 wherein the aqueous emulsion of cajeput oil is added to the water on the basis of an amount of about 0.001 ml to about 1 ml of cajeput oil per day per 10 gallons of water.

5. The method according to claim 1 wherein the aqueous emulsion of cajeput oil is added to the water on the basis of an amount from about 0.01 ml to about 0.5 ml of cajeput oil per day per 10 gallons of water.

6. The method according to claim 1 wherein the emulsion further comprises an emulsifier, in an amount sufficient to form a stable aqueous emulsion of cajeput oil in water.

7. The method according to claim 6 wherein the emulsion comprises from about 0.1% to about 20% by volume cajeput oil in water and about 0.01% to about 20% by volume emulsifier, the amounts based on the total volume of the emulsion.

8. The method according to claim 6 wherein the emulsion comprises about 0.5% to about 10% by volume cajeput oil and about 0.1% to about 5% by volume emulsifier, the amounts based on the total volume of the emulsion.

9. The method according to claim 6 wherein the emulsion comprises about 1% by volume cajeput oil and about 1% by volume emulsifier, the amounts based on the total volume of the emulsion.

10. The method according to claim 1 wherein the emulsion further comprises a defoamer in an amount sufficient to control foaming during preparation of the emulsion.

11. The method according to claim 7 wherein the emulsion further comprises a defoamer present in an amount of less than about 5% by volume, based on the total volume of the emulsion.

12. The method according to claim 8 wherein the emulsion further comprises a defoamer present in an amount of less than about 1% by volume, based on the total volume of the emulsion.

13. The method according to claim 9 wherein the emulsion further comprises a defoamer present in an amount of about 0.2% by volume, based on the total volume of the emulsion.

14. The method according to claim 13, wherein the emulsion is added to the water in an amount of about 5 ml per day per 10 gallons of water.

15. The method according to claim 1 wherein the living aquatic animal is a fish.

16. A prophylactic method for treating a living, disease-free aquatic animal which comprises adding to water containing the living aquatic animal an aqueous emulsion of cajeput oil in an amount effective to promote resistance of the living aquatic animal to disease.

17. The prophylactic method of claim 16 wherein the aqueous emulsion is added to the water on the basis of about 0.001 ml to about 1 ml of cajeput oil per day per 10 gallons of water.

18. The prophylactic method according to claim 16 wherein the living aquatic animal is a fish.

19. A composition for treating a living aquatic animal which comprises a stable aqueous emulsion comprising about 0.1% to about 20% by volume cajeput oil in water, based on the total volume of the composition, an emulsifier in an amount of about 0.01% to about 20% by volume sufficient to form a stable emulsion of the cajeput oil in the water, and a defoamer in an amount less than about 5% by volume sufficient to control foaming during preparation of the composition.

20. The composition of claim 19 wherein the emulsifier is a nonionic emulsifier.

21. The composition of claim 19 wherein the emulsion comprises about 0.5% to about 10% by volume cajeput oil.

22. The composition of claim 19 wherein the emulsion comprises about 1% to about 5% by volume cajeput oil, about 0.1% to about 5% by volume emulsifier and less than about 1% by volume defoamer.

23. A composition according to claim 19 wherein the emulsion comprises about 1% by volume cajeput oil, about 1% by volume emulsifier and about 0.2% by volume defoamer.

* * * * *